(12) United States Patent
Criscione et al.

(10) Patent No.: US 10,507,271 B2
(45) Date of Patent: Dec. 17, 2019

(54) FULLY IMPLANTABLE DIRECT MYOCARDIUM ASSIST DEVICE

(71) Applicants: THE TEXAS A&M UNIVERSITY SYSTEM, College Station, TX (US); CorInnova Incorporated, Houston, TX (US)

(72) Inventors: John C. Criscione, College Station, TX (US); Boris Leschinsky, Mahwah, NJ (US)

(73) Assignees: CorInnova Incorporated, Houston, TX (US); The Texas A&M University System, College Station, TX (US)

( * ) Notice: Subject to any disclaimer, the term of this patent is extended or adjusted under 35 U.S.C. 154(b) by 12 days.

(21) Appl. No.: 15/631,708

(22) Filed: Jun. 23, 2017

(65) Prior Publication Data
US 2017/0368246 A1    Dec. 28, 2017

Related U.S. Application Data

(60) Provisional application No. 62/353,834, filed on Jun. 23, 2016.

(51) Int. Cl.
*A61M 1/12* (2006.01)
*A61M 1/10* (2006.01)

(52) U.S. Cl.
CPC .......... *A61M 1/122* (2014.02); *A61M 1/1037* (2013.01); *A61M 1/107* (2013.01); *A61M 1/1046* (2013.01); *A61M 1/1067* (2013.01)

(58) Field of Classification Search
CPC ................. A61N 1/362; A61B 17/00
See application file for complete search history.

(56) References Cited

U.S. PATENT DOCUMENTS

| 2,826,193 A | 3/1958 | Vineberg |
| 3,034,501 A | 5/1962 | Hewson |

(Continued)

FOREIGN PATENT DOCUMENTS

| WO | 1999022784 A1 | 5/1999 |
| WO | 2000036995 A2 | 6/2000 |

(Continued)

OTHER PUBLICATIONS

Anstadt, et al., "Non-blood contacting biventricular support for severe heart failure." Ann Thorac Surg (2002), 73:556-62.

(Continued)

*Primary Examiner* — Yashita Sharma
(74) *Attorney, Agent, or Firm* — Chainey P. Singleton

(57) ABSTRACT

The present invention provides an implantable cardiac compression device comprising: an inflatable cardiac compression jacket configured when inflated to directly compress a heart and assist in displacing blood therefrom, a channel that connects the inflatable cardiac compression jacket and an expandable fluid reservoir configured to contain a fluid when displaced compresses the inflatable cardiac compression jacket, and a fluid driver operably connected to the inflatable cardiac compression jacket and to the expandable fluid reservoir, wherein the fluid driver is configured to inflate the cardiac compression jacket and to deflate the expandable fluid reservoir during systole of the heart; said driver is further configured to deflate the cardiac compression jacket and to inflate the expandable fluid reservoir during diastole of the heart.

13 Claims, 8 Drawing Sheets

(56) References Cited

U.S. PATENT DOCUMENTS

| | | |
|---|---|---|
| 3,233,607 A | 2/1966 | Bolie |
| 3,513,836 A | 5/1970 | Sausse |
| 4,048,990 A | 9/1977 | Goetz |
| 4,185,617 A | 1/1980 | Hutchins |
| 4,536,893 A | 8/1985 | Parravicini |
| 4,685,446 A | 8/1987 | Choy |
| 5,089,017 A | 2/1992 | Young et al. |
| 5,119,804 A | 6/1992 | Anstadt |
| 5,131,905 A | 7/1992 | Grooters |
| 5,169,381 A | 12/1992 | Snyders |
| 5,256,132 A | 10/1993 | Snyders |
| 5,348,528 A | 9/1994 | Vince |
| 5,483,958 A | 1/1996 | Merberg et al. |
| 5,562,730 A | 10/1996 | Davidson |
| 5,627,630 A | 5/1997 | Matsumae et al. |
| 5,713,954 A | 2/1998 | Rosenberg et al. |
| 5,738,627 A | 4/1998 | Kovacs et al. |
| 5,749,839 A | 5/1998 | Kovacs |
| 5,863,574 A | 1/1999 | Julien |
| 6,155,968 A | 12/2000 | Wilk |
| 6,224,540 B1 | 5/2001 | Lederman et al. |
| 6,293,906 B1 | 9/2001 | Vanden Hoek et al. |
| 6,387,042 B1 | 5/2002 | Herrero |
| 6,540,666 B1 | 4/2003 | Chekanov |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,978 B2 | 9/2003 | Lau et al. |
| 6,612,979 B2 | 9/2003 | Lau et al. |
| 6,626,821 B1 | 9/2003 | Kung et al. |
| 6,663,558 B2 | 12/2003 | Lau et al. |
| 6,685,627 B2 | 2/2004 | Jayaraman |
| 6,723,039 B2 | 4/2004 | French et al. |
| 6,784,283 B2 | 8/2004 | Andersen et al. |
| 7,097,611 B2 | 8/2006 | Lau et al. |
| 7,229,405 B2 | 6/2007 | Lau et al. |
| 7,275,542 B2 | 10/2007 | Lurie et al. |
| 7,445,593 B2 | 11/2008 | Criscione |
| 7,489,380 B2 | 2/2009 | Lim et al. |
| 7,494,459 B2 | 2/2009 | Anstadt et al. |
| 7,674,222 B2 | 3/2010 | Nikolic et al. |
| 7,871,366 B2 | 1/2011 | Criscione et al. |
| 7,935,045 B2 | 5/2011 | Criscione et al. |
| 8,011,367 B2 | 9/2011 | Lurie et al. |
| 8,075,471 B2 | 12/2011 | Trumble |
| 8,187,160 B2 | 5/2012 | Criscione et al. |
| 8,192,351 B2 | 6/2012 | Fishier et al. |
| 8,550,976 B2 | 10/2013 | Criscione |
| 8,944,986 B2 | 2/2015 | Altman et al. |
| 9,259,520 B2 | 2/2016 | Altman et al. |
| 9,510,746 B2 | 12/2016 | Criscione et al. |
| 2002/0007216 A1 | 1/2002 | Melvin |
| 2002/0065449 A1 | 5/2002 | Wardle |
| 2003/0088151 A1 | 5/2003 | Kung et al. |
| 2004/0010180 A1 | 1/2004 | Scorvo |
| 2004/0167376 A1* | 8/2004 | Peters ............ A61M 1/1037 600/18 |
| 2005/0004420 A1 | 1/2005 | Criscione |
| 2005/0187425 A1 | 8/2005 | Alferness et al. |
| 2005/0217677 A1 | 10/2005 | Lurie et al. |
| 2006/0241334 A1 | 10/2006 | Dubi et al. |
| 2006/0276683 A1 | 12/2006 | Feld et al. |
| 2006/0287568 A1 | 12/2006 | Jassawalla et al. |
| 2007/0015958 A1 | 1/2007 | Lau et al. |
| 2007/0016184 A1 | 1/2007 | Cropper et al. |
| 2007/0161846 A1 | 7/2007 | Nikolic et al. |
| 2007/0208214 A1 | 9/2007 | Hjelle et al. |
| 2007/0221222 A1 | 9/2007 | Lurie |
| 2007/0276444 A1 | 11/2007 | Gelbart et al. |
| 2008/0004488 A1 | 1/2008 | Hjelle et al. |
| 2008/0021260 A1 | 1/2008 | Criscione et al. |
| 2008/0021266 A1 | 1/2008 | Laham et al. |
| 2008/0071134 A1 | 3/2008 | Dubi et al. |
| 2008/0257344 A1 | 10/2008 | Lurie et al. |
| 2009/0036730 A1 | 2/2009 | Criscione et al. |
| 2009/0043152 A1 | 2/2009 | Lau et al. |
| 2009/0062701 A1 | 3/2009 | Yannopoulos et al. |
| 2009/0118570 A1 | 5/2009 | Harrison et al. |
| 2009/0318746 A1 | 12/2009 | Thurmond, II et al. |
| 2010/0081867 A1 | 4/2010 | Fishier et al. |
| 2010/0152531 A1 | 6/2010 | Goodman et al. |
| 2010/0249519 A1 | 9/2010 | Park et al. |
| 2011/0021864 A1 | 1/2011 | Criscione et al. |
| 2011/0034776 A1 | 2/2011 | Dixon et al. |
| 2011/0040152 A1 | 2/2011 | Kim et al. |
| 2011/0166410 A1 | 7/2011 | Gutierrez et al. |
| 2013/0102849 A1 | 4/2013 | Criscoine et al. |
| 2013/0150923 A1 | 6/2013 | Schnetz et al. |
| 2014/0194671 A1* | 7/2014 | Wildhirt ............ A61M 1/122 600/17 |
| 2015/0165104 A1 | 6/2015 | Criscione et al. |
| 2017/0014233 A1 | 1/2017 | Criscione et al. |

FOREIGN PATENT DOCUMENTS

| | | |
|---|---|---|
| WO | 2003001971 A2 | 1/2003 |
| WO | 2004112867 A1 | 12/2004 |
| WO | 2006108177 A2 | 10/2006 |
| WO | 2007062239 A2 | 5/2007 |
| WO | 2008154033 A2 | 12/2008 |
| WO | 2009018358 A2 | 2/2009 |
| WO | 2011011641 A2 | 1/2011 |
| WO | 2011011642 A2 | 1/2011 |
| WO | 2012000003 A1 | 1/2012 |
| WO | 2012075460 A2 | 6/2012 |
| WO | 2012094064 A1 | 7/2012 |
| WO | 2013059316 A2 | 4/2013 |
| WO | 2014030140 A1 | 2/2014 |
| WO | 2016176431 A1 | 11/2016 |
| WO | 2017011778 A1 | 1/2017 |

OTHER PUBLICATIONS

Artrip, et al., "Physiological and hemodynamic evaluation of non-uniform direct cardiac compression." Circulation (1999), 100 (suppl II):236-43.

Cohn, et al. "Cardiac Remodeling-Concepts and Clinical Implications: A Consensus Paper From an International Forum on Cardiac Remodeling" Journal of the American College of Cardiology vol. 35, No. 3, Mar. 1, 2000.

Cooley, et al. "The past 50 years of cardiovascular surgery" (2000) Circulation 102: IV88-93.

Dipla, et al., "Myocyte recovery after mechanical circulatory support in humans with end-stage heart failure." Circulation (1998), 97:2316-2322.

European Patent Office, Partial Supplementary European Search Report for EP 12841226.9 (PCT/US2012/060609), dated Jun. 9, 2015.

European Patent Office, European Search Report for EP 12841226.9 (PCT/US2012/060609), dated Dec. 14, 2015.

Feldman, et al. "Selective changes in cardiac gene expression during compensated hypertrophy and the transition to cardiac decompensation in rats with chronic aortic banding" (Jul. 1993). Circ. Res. 73: 184-192.

Ghanta, et al, "Adjustable, Physiological Ventricular Restraint Improves Left Ventricular Mechanics and Reduces Dilation in an Ovine Model of Chronic Heart Failure," Mar. 13, 2007, Circuilation (10):12-1-10.

Ghanta, et al, "Real-time Adjustment of Ventricular Restraint Therapy in Heart Failure," Dec. 2008, Eur. J. Cardiothorac Surg., 34(6):1136-40, available online Aug. 19, 2008.

Gheorhiad, et al. "Chronic Heart Failure in the United States: A Manifestation of Coronary Artery Disease" (1998) Circulation 97:282-9.

Goldstein, et al., "Medical progress: implantable left ventricular assist devices." N Engl J Med (Nov. 19, 1998), 339 (21):1522-1533.

Heerdt, et al., "Chronic unloading by left ventricular assist device reverses contractile dysfunction and alters gene expression in end-stage heart failure." Circulation (2000), 102:2713-2719.

(56) References Cited

OTHER PUBLICATIONS

Karvarana, et al., "Circulatory support with a direct cardiac compression device: a less invasive approach with the AbioBooster device." J Thorac Cardiovasc Surg, (Oct. 2001), 122:786-787.

Kawaguchi, et al., "Mechanical enhancement of myocardial oxygen saving by synchronized dynamic left ventricular compression." J Thorac Cardiovasc Surg (1992), 103:573-81 (Abstract Only).

Kherani, et al., "Ventricular assist devices as a bridge to transplant or recovery" Cardiol (2004), 101:93-103.

Machine Translation of WO 2012/000003 (PCT/AT2011/000218)—Publication date Jan. 5, 2012—Abstract, description & claims, 21 pp.

Mann, et al, "Mechanisms and Models in Heart Failure: the Biomechanical Model and Beyond," May 31, 2005, Circulation, 111(21):2837-49.

Mann, et al, "Left Ventricular Size and Shape: Determinants of Mechanical Signal Transduction Pathways," 2005, Heart Failure Reviews, vol. 10, No. 2, pp. 95-100.

Moreno, et al, "Assessment of Minimally Invasive Device That Provides Simultaneous Adjustable Cardiac Support and Active Synchronous Assist in an Acute Heart Failure Model," Journal of Medical Devices, Dec. 2011, vol. 5 / 041008-1.

Omens, J.H. "Stress and strain as regulators of myocardial growth." Prog. Biophys. Molec. Biol. (1998), 69:559-572.

Oz, et al., "Direct cardiac compression devices." J Heart Lung Transplant (Oct. 2002), 21:1049-1055.

Rose, et al., "Long-term use of left ventricular assist device for end-stage heart failure." N Engl J Med (Nov. 15, 2001), 345(20):1435-1443.

Snowden, et al. "Modulation of Diastolic Filling Using an Epicardial Diastolic Recoil Device" Journal of Medical Devices Sep. 2013, vol. 7 / 034503-1.

Tamminen, et al., "Ectopic Expression of AB13 Gene Enhances Freezing Tolerance in Response to Abscisic Acid and Low Temperature in *Arabidopsis thaliana*," The Plant Journal, (2001), 25(1):1-8.

Williams, et al. "Direct cardiac compression for cardiogenic shock with the CardioSupport System." Ann Thorac Surg (2001), 71:S188-9.

United States Patent & Trademark Office (ISA), International Search Report and Written Opinion for PCT/US2005/003343 dated Jul. 16, 2007.

United States Patent & Trademark Office (ISA), International Search Report and Written Opinion for PCT/US2016/029756 dated Jul. 27, 2016.

United States Patent & Trademark Office (ISA), International Search Report and Written Opinion for PCT/US2016/042578 dated Oct. 19, 2016.

European Patent Office, Supplementary European Search Report for EP 10802924.0 (PCT/US2010/042970), dated Sep. 27, 2012.

European Patent Office (ISA), Written Opinion for PCT/US2004/019809 dated Oct. 24, 2005—8 pp.

Korean Intellectual Property Office (ISA), International Search Report for PCT/US2010/042970, dated May 2, 2011, 13 pp.

Korean Intellectual Property Office (ISA), International Search Report and Written Opinion for PCT/US2010/042972, dated Apr. 14, 2011, 8 pp.

Korean Intellectual Property Office (ISA), International Search Report for PCT/US2008/071618 dated Feb. 12, 2009.

United States Patent & Trademark Office (ISA) (Corrected), International Search Report and Written Opinion for PCT/US2006/013457 dated Dec. 10, 2007.

Korean Intellectual Property Office (ISA), International Search Report and Written Opinion for PCT/US2011/063178 dated Jun. 25, 2012—14 pp.

Korean Intellectual Property Office (ISA), International Search Report and Written Opinion for PCT/US2012/060609 dated Apr. 19, 2013—15 pp.

* cited by examiner

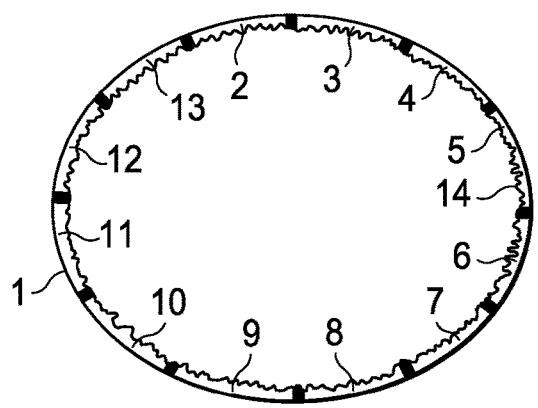
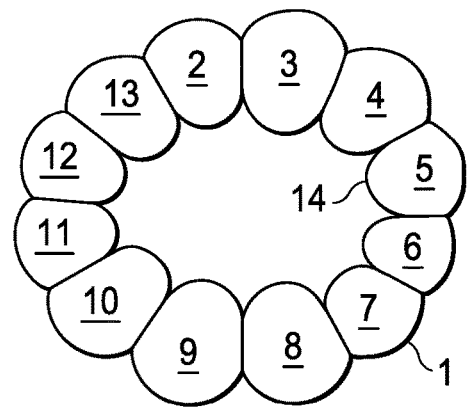
FIG. 1A
FIG. 1B
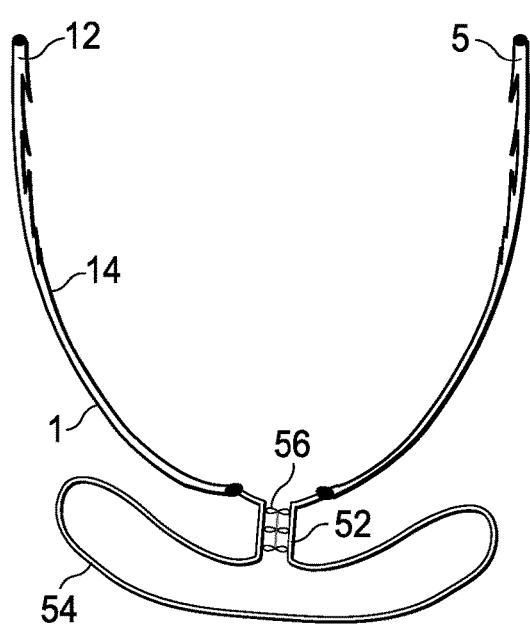
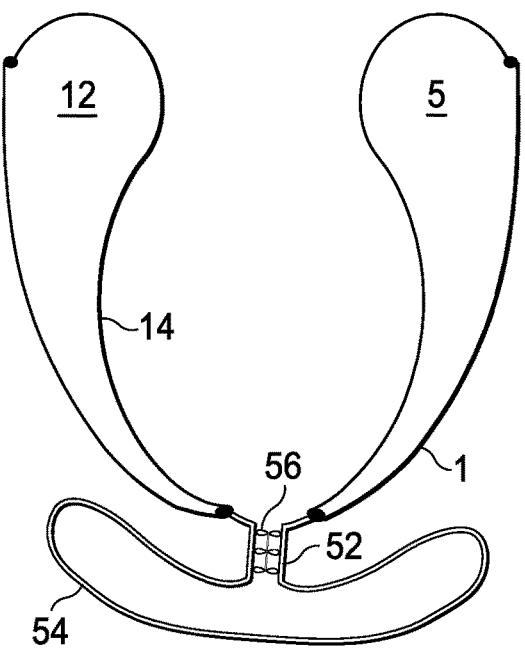
FIG. 2A
FIG. 2B

FULLY IMPLANTABLE DIRECT MYOCARDIUM ASSIST DEVICE

CROSS-REFERENCE TO RELATED APPLICATIONS

This application claims benefit of U.S. Provisional Application Ser. No. 62/353,834 filed Jun. 23, 2016 which is incorporated herein by reference in its entirety.

TECHNICAL FIELD OF THE INVENTION

The present invention relates in general to the field of heart assist devices, and more particularly, to a fully implantable device for cardiac compression.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with a fully implantable device for cardiac compression. During a cardiac cycle, the heart expels oxygenated blood into the aorta as its left ventricle contracts (i.e., during systole) and, thereafter, receives a backflow of arterial blood into the coronary arteries as its left ventricle relaxes (i.e., during diastole). The systolic pumping of blood into the aorta requires the myocardium to overcome the static pressure of blood that is already in the aorta. A healthy heart is typically able to perform both of these functions effectively. However, a weakened or failing heart may be unable to perform the work required to fully overcome the static pressure of blood already in the aorta, thereby resulting in less ejection of oxygenated blood into the aorta during systole and less backflow of oxygenated blood into the coronary arteries during diastole. There are various methods of providing assistance to the failing myocardium.

Direct cardiac compression devices are generally known as disclosed first by Anstadt and later by Criscione and are effective in providing assistance to the failing myocardium by generally adding external pressure to help the heart muscle to contract. Generally these devices include a jacket positioned around the heart and containing inflatable bladders that are inflated to coincide with contraction of the myocardium during systole. Operation of such device is supported by a driver configured to inject fluid through a drive line to cause the bladders to expand and withdrawal of fluid during diastole causes the bladders to collapse in preparation for the next systole of the heart. The presence of the drive line exiting the subject is generally undesirable as it may be a source of infection, especially for patients requiring long-term or permanent support. One difficulty associated with injecting and removing a certain volume of drive fluid is the changing volume of the drive system. This changing volume of the drive system makes an implantable driver with changing internal volume problematic, due to the positioning of the device inside the subject so as to not periodically compress surrounding tissues.

U.S. Pat. No. 4,813,952 entitled, "Cardiac Assist Device," discloses a muscle-powered pump to assist the natural heart, the entire contents of which are incorporated herein by reference. The device comprises an oblate, spheroidal-shaped pumping chamber surrounded by innervated muscular tissue. The device may be coupled to the ventricle and descending aorta with valves and be stimulated in synchrony with the natural depolarization of the heart or the device may be inserted into the descending aorta and used as a counterpulsation device. In this application, the innervated muscle is stimulated after a brief delay from the natural cardiac depolarization.

U.S. Patent Publication No. 2007/0129796 entitled, "Actuator for a heart assist device," discloses an actuator for a heart assist device having an inflatable balloon and a shroud or wrap.

SUMMARY OF THE INVENTION

The present inventors recognized a long felt but unresolved need for a device with maximal degree of assistance to the heart and the circulatory system that uses a fully implantable driver so as to minimize the risk of infection when such device is used over an extended period of time.

The present invention provides an implantable cardiac compression device comprising: an inflatable cardiac compression jacket configured when inflated to directly compress a heart and assist in displacing blood therefrom, a channel that connects the inflatable cardiac compression jacket and an expandable fluid reservoir configured to contain a fluid when displaced from the inflatable cardiac compression jacket, and a fluid driver operably connected to the inflatable cardiac compression jacket and to the expandable fluid reservoir, wherein the fluid driver is configured to inflate the cardiac compression jacket and to deflate the expandable fluid reservoir during systole of the heart; the driver is further configured to deflate the cardiac compression jacket and to inflate the expandable fluid reservoir during diastole of the heart.

The present invention provides an implantable cardiac compression device comprising: an inflatable cardiac compression device comprising a resilient inner panel in contact with a heart periphery comprising one or membranes contoured to provide curvatures generally in the shape of the heart to affect the end-diastolic heart volume, an inflatable outer panel comprising one or more inflatable membranes positioned at least partially around the resilient inner panel to inflate to affect the end-systolic heart volume, and a fluid connection in communication with the inflatable outer panel for inflation and deflation; an expandable fluid reservoir in communication with the fluid connection and configured to contain a fluid when displaced from the inflatable cardiac compression jacket, and a fluid driver operably connected to the inflatable cardiac compression jacket and to the expandable fluid reservoir, wherein the fluid driver is configured to fill the cardiac compression jacket with the fluid at least partially removed from the expandable fluid reservoir during systolic ejection by the heart and is further configured to fill the expandable fluid reservoir with fluid at least partially removed from the cardiac compression jacket during diastolic filling of the heart.

The flexible membrane may be substantially inelastic. The fluid may be disposed within the expandable fluid reservoir. The inflatable cardiac compression device may include four to eight at least partially overlapped membranes connected to form a continuous outer edge. The resilient inner panel, the inflatable outer panel or both may comprise an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof. The cardiac compression jacket may further comprise one or more resilient members which in turn comprise individually a metal, an alloy, a memory metal, a composite, a polymer, a plastic, a memory plastic, strands, yarns, strips, or a combination thereof. The cardiac compression jacket may further comprise one or more sensors, one or more electrodes to sense native electrocardiogram (ECG), provide pacing stimuli to the heart, one or more electrodes to provide an electrical shock to the heart for defibrillation, one or more electrodes to provide an electrical stimulus to the heart, or a combination thereof in contact with the compression cardiac device. The cardiac compression jacket, the expandable fluid reservoir or both may comprise one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof. Such bioactive agents may be positioned on a surface of the above mentioned parts of the device.

The present invention provides a method of periodically compressing the heart using an implantable cardiac compression device comprising the steps of:

a. providing an inflatable cardiac compression device comprising a resilient inner panel in contact with a heart periphery, such inner panel comprising one or membranes contoured to provide curvatures generally in the shape of the heart to affect the end-diastolic heart volume, an inflatable outer panel comprising one or more inflatable membranes positioned at least partially around the resilient inner panel to affect the end-systolic heart volume, and a fluid connection in communication with the inflatable outer panel for inflation and deflation; an expandable fluid reservoir in communication with the fluid connection and configured to contain a fluid;

b. controlling the fluid driver to move the fluid from the expandable fluid reservoir to the inflatable direct cardiac compression jacket, wherein the fluid is displaced and fills the inflatable cardiac compression jacket to compress the heart; and c. controlling the fluid driver to move the fluid from the inflatable direct cardiac compression jacket to the expandable fluid reservoir wherein the fluid is displaced and fills the expandable fluid reservoir to relax the inflatable cardiac compression jacket.

The method may further comprise the step of controlling the fluid driver to provide a compression-decompression rhythm. The method may include a driver controller in communication with the fluid driver to control the direction of the motor to control the compression and decompression of the heart. The flexible membrane may be substantially inelastic. The inflatable cardiac compression device may include eight at least partially overlapped membranes connected to form a continuous outer edge. The resilient inner panel, the inflatable outer panel or both may be an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

The cardiac compression jacket further may include one or more resilient members comprise individually a metal, an alloy, a memory metal, a composite, a polymer, a plastic, a memory plastic, strands, yarns, strips, or a combination thereof. The cardiac compression jacket further comprises one or more sensors, one or more electrodes to provide pacing stimuli to the heart, one or more electrodes to provide an electrical shock to the heart for defibrillation, one or more electrodes to provide an electrical stimuli to the heart, or a combination thereof in contact with the compression cardiac device. The cardiac compression jacket, the expandable fluid reservoir or both may include one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

BRIEF DESCRIPTION OF THE DRAWINGS

For a more complete understanding of the features and advantages of the present invention, reference is now made to the detailed description of the invention along with the accompanying figures and in which:

FIGS. 1A-1B are schematic diagrams of the cross-section, top down view, of a device according to one embodiment of the present invention without a heart inside, wherein FIG. 1A is in the deflated state and FIG. 1B is in the pressurized state;

FIGS. 2A-2B are schematic diagrams of the long-section of a device according to one embodiment of the present invention without a heart inside, wherein FIG. 2A is in the deflated state and FIG. 2B is in the pressurized state;

FIGS. 3A-3B are schematic diagrams of the cross-section of a device according to one embodiment of the present invention with a heart inside, wherein FIG. 3A is in the deflated state and FIG. 3B is in the pressurized state;

FIGS. 4A-4B are schematic diagrams of the long-section of a device according to an embodiment of the present invention with a heart inside, wherein FIG. 4A is in the deflated state and FIG. 4B is in the pressurized state;

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Though different devices exist today with specific indications for medium/long term support, the present invention is a significant innovation in the cardiac device industry, as it can address both systolic and diastolic heart failure with a single device design. The present invention minimizes infection, and a need for anticoagulation. Heart replacement is highly invasive and induces great trauma on the patient and complications from anti-rejection medication. Current, blood-contacting assist technologies provide greater risk factors for blood trauma, clotting activation, and sepsis. Blood-contacting assist technologies cannot be started and stopped because of a risk of clot formation. The present invention can be used in combination therapies which combine mechanical, electrical, pharmaceutical, and/or stem cell therapies.

Figure 9:
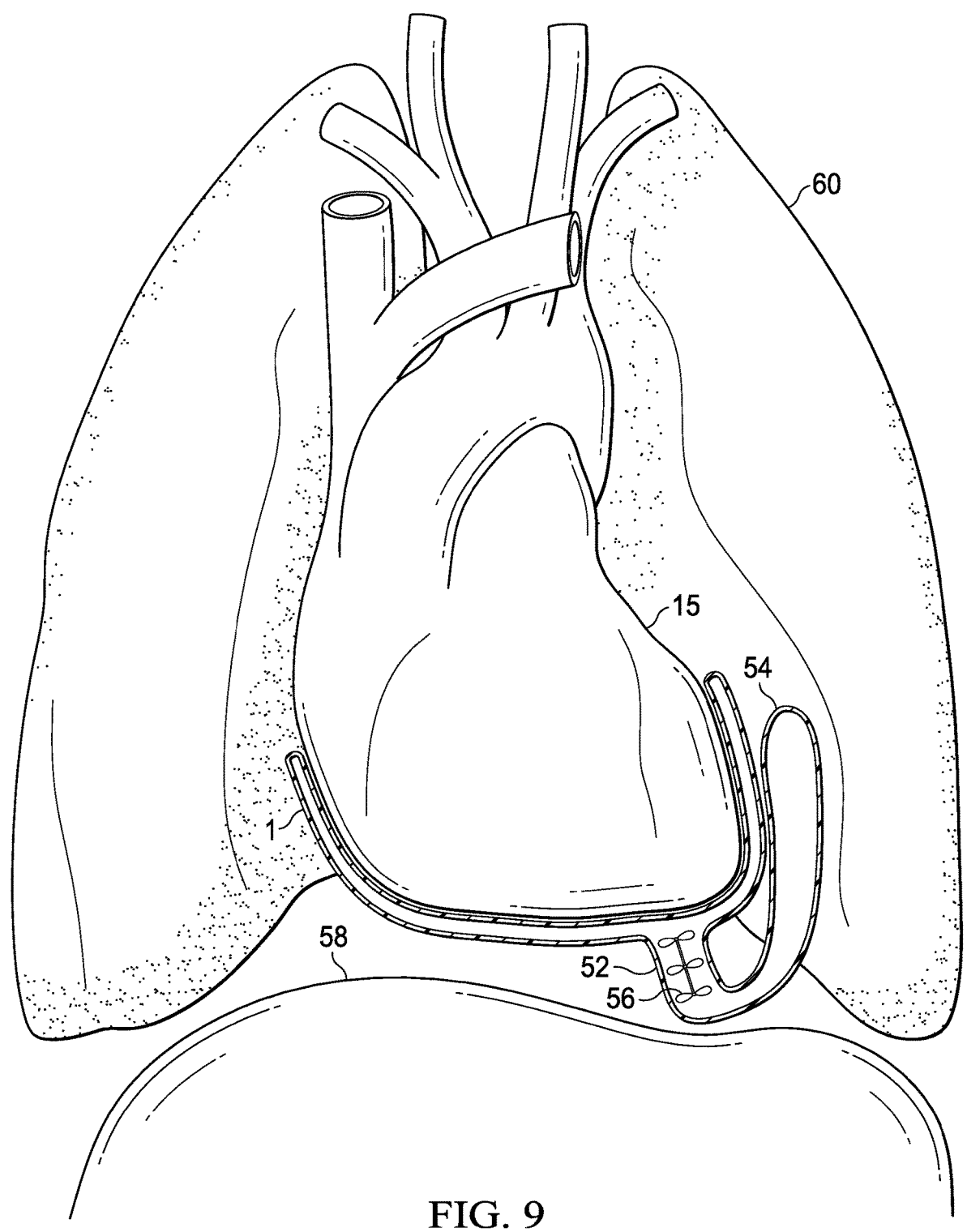
FIG. 9 illustrates a cardiac compression device that includes a cardiac compression device, channel and fluid reservoir that is positioned on the lateral margin of the pericardial sac between the heart and the lung.

The present invention provides a fully implantable device for direct cardiac compression and aortic compression. Any direct cardiac compression device may be used in conjunction with the present invention from the Anstadt cup as illustrated in FIG. 9 of the Anstadt patent (U.S. Pat. No. 5,119,804) to a contoured diastolic recoil device as seen in U.S. Pat. No. 8,944,986 and U.S. Provisional Patent Application Ser. Nos. 61/271,559 and 61/276,215.

The present invention includes a cardiac compression device that is fully implantable and includes at least 2 connected portions. The first portion is a compression cup that is positioned around the heart or a portion of the heart to compress the heart. The second portion of the device is a fluid reservoir that holds a fluid. The first and second portions are connected to allow the transfer of fluid from the fluid reservoir to the compression cup to compress the compression cup and in turn compress the heart and to allow the transfer of fluid from the compression cup to the fluid reservoir to remove pressure from the compression cup and in turn remove pressure from the heart. The compression cup and the fluid reservoir may include a fluid driver that pumps the fluid into and out of the fluid reservoir.

One embodiment of the cardiac compression device used in the present invention is the Anstadt cup or cup design that presses in on the heart. The cup may include one or more bladders that may be individually inflated or deflated to achieve the desired purpose. Another embodiment of the cardiac compression device includes a selectively inflatable end-systolic heart shaped bladder with one or more contoured supports configured to surround at least a portion of the heart to provide curvatures similar to the proper shape of the heart when pressurized and one or more fluid connections in communication with the selectively inflatable end-systolic heart shaped bladder for pressurization and depressurization. The one or more contoured supports form one or more inflatable compartments having an expanded curvature optimized to fit generally the proper end-systolic shape of the heart. The selectively inflatable end-systolic heart shaped bladder includes an inner membrane that is at least partially folded when depressurized; and at least partially unfolded when pressurized. In another embodiment, the selectively inflatable end-systolic heart shaped bladder includes an inner membrane that is at least partially folded when depressurized and at least partially unfolded when pressurized; and an outer membrane that is at least partially folded when depressurized; and at least partially unfolded when pressurized. Other embodiments may include various combinations thereof. The one or more contoured supports may include one or more dividers individually of similar or different materials, one or more wires individually of similar or different materials or a combination thereof to form a shape generally appropriate to the proper end-systolic shape of the heart. The selectively inflatable end-systolic heart shaped bladder includes a material that is substantially biocompatible, fluid-impermeable and substantially flexible. For example, at least a portion of the device may be made from elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof. The selectively inflatable end-systolic heart shaped bladder is generally collapsible when depressurized and is reinforced to resist radially outward expansion during pressurization. The device of the present invention may take many configurations depending on the particular treatment. For example, the selectively inflatable end-systolic heart shaped bladder may include 12 inflatable tapered compartments formed by the one or more contoured supports to provide an expanded curvature similar to the proper end-systolic shape of the heart; however, other embodiments may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more inflatable tapered compartments. Furthermore, the distribution of the inflatable tapered compartments may vary from the design of 4 chambers on the right ventricle (RV) side and 8 chambers that are mostly on the left ventricle (LV) but also overlapping the interventricular sulci. For example, the device may have 1, 2, 3, 4, 5, 6, 7, 8, 9, 10, 11, 12 or more chambers on the RV side and 1, 2, 3, 4, 5, 6, 7, 8, 9, 10, 11, 12, 13, 14, 15, 16, 17, 18, 19, 20, 21, 22, 23, 24 or more chambers that are mostly on the LV and overlapping the interventricular sulci. That chambers distribution determination for a particular application and treatment is within the scope of the skilled artisan. The inflatable tapered compartments are connected to a pneumatic pressure source through an inlet port and an outlet port. The device is inflated with a positive pressure during systole and deflated via suction during diastole. Although, other configurations and multiple connections are also possible depending on the particular application and configuration. The inlet port and an outlet port may be connected through a single connection for applying the positive pressure and the suction or negative pressure; alternatively, multiple connections may be used. In addition, the inlet port and an outlet port may be made anywhere about the boundary of the selectively inflatable end-systolic heart shaped bladder, e.g., near the base or near the apex.

One embodiment of the cardiac compression device applies forces to the exterior, epicardial boundary of the heart to restrict inflow and modulate right flow versus left flow through the heart. The device includes a selectively inflatable end-diastolic contoured bladder having one or more contoured supports configured to releasably engage the heart. The one or more contoured supports protrude inward towards the right ventricle to decrease the end-diastolic volume of the right ventricle during diastole. The device also has an inlet connection and outlet connection in communication with the selectively inflatable end-diastolic contoured bladder to pressurize and depressurize the selectively inflatable end-diastolic contoured bladder. Residual pressure is applied about the right ventricle to not fully deflate during diastole.

Generally, the inlet line is in communication with the inlet connection to operatively expand the selectively inflatable end-diastolic contoured bladder and an outlet line is in communication with the outlet connection to operatively withdraw fluid from the selectively inflatable end-diastolic contoured bladder. This allows connection to conventional devices to apply and remove pressure or custom devices designed specifically for the present invention.

One embodiment of the cardiac compression device is a soft-shelled device that has inflatable, longitudinally oriented chambers that when deflated are collapsible, allowing for minimally invasive implantation. In addition, the deflated chambers are shaped and adjoined to form a structure that allows typical diastolic configurations. When pressurized the chambers push on the exterior of the heart in such a way as to induce a systolic configuration with normal curvatures.

FIGS. 1A and 1B illustrate a horizontal cross section of one embodiment of the direct cardiac compression device 1 of the present invention in the deflated state, as seen in FIG. 1A and the inflated state in FIG. 1B. The direct cardiac compression device 1 includes 12 chambers 2-13 arranged with 4 chambers on the RV side and 8 chambers that are mostly on the LV but also overlapping the interventricular sulci. The chambers 2-13 are constructed from polyurethane film in one embodiment; however, other materials may be used. The sides of the chambers 2-13, which are on the outer boundary, form a shape that is similar to the end diastolic shape of the heart. The interior surface 14 has folds and crenulations such that when inflated the chambers 2-13 mostly expand inward.

FIGS. 2A and 2B illustrate a vertical cross-section of one embodiment of the cardiac compression device 1 of the present invention in the deflated state as seen in FIG. 2A and the inflated state in FIG. 2B. Cardiac compression device 1 includes chambers 5 and 12 in the inflated and deflated states using channel 52 that connects to the fluid reservoir 54. The fluid driver 56 is located in the channel 52 to flow fluid into the cardiac compression device 1 from the fluid reservoir 54 and from the fluid reservoir 54 into the cardiac compression device 1. The interior surface 14 of the chambers 2-13 (not shown) that are on the outer boundary form a shape that is similar to the end diastolic shape of the heart. The interior surface 14 has folds and crenulations such that when inflated the chambers 2-13 mostly expand inward to contact the epicardium 16 (not shown) of the heart 15 (not shown).

Figure 3A:
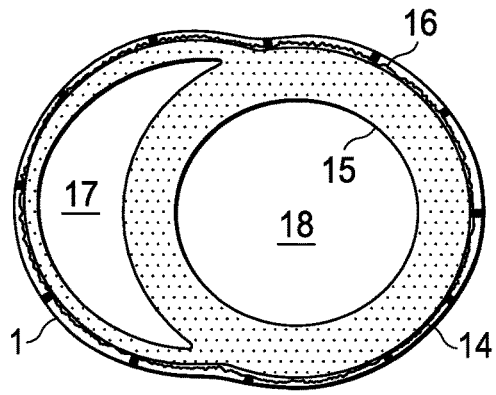
Figure 3B:
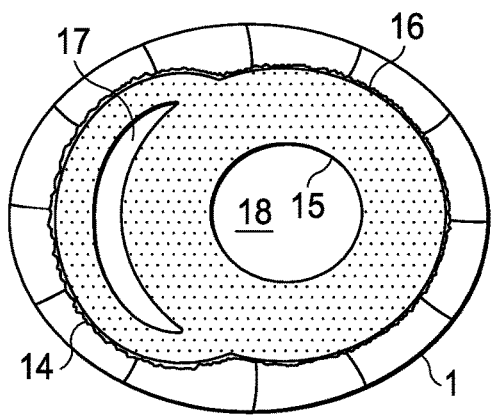

FIGS. 3A and 3B illustrate a horizontal cross-section of one embodiment of the cardiac compression device 1 of the present invention fitted to the heart 15. FIG. 3A is in the deflated state and FIG. 3B is in the inflated state. The cardiac compression device 1 includes 12 chambers 2-13 arranged with 4 chambers on the RV side and 8 chambers that are mostly on the LV but also overlapping the interventricular sulci. The chambers 2-13 include interior surface 14 that contacts the epicardium 16 of the heart 15. The side of the chambers 2-13 that are on the outer boundary form a shape that is similar to the end diastolic shape of the heart. The interior surface 14 has folds and crenulations such that when inflated the chambers 2-13 mostly expand inward. The shape of the interior regions 17, 18, of the heart 15, can be compared in the inflated state as seen in FIG. 3B and the deflated state in FIG. 3A.

Figure 4A:
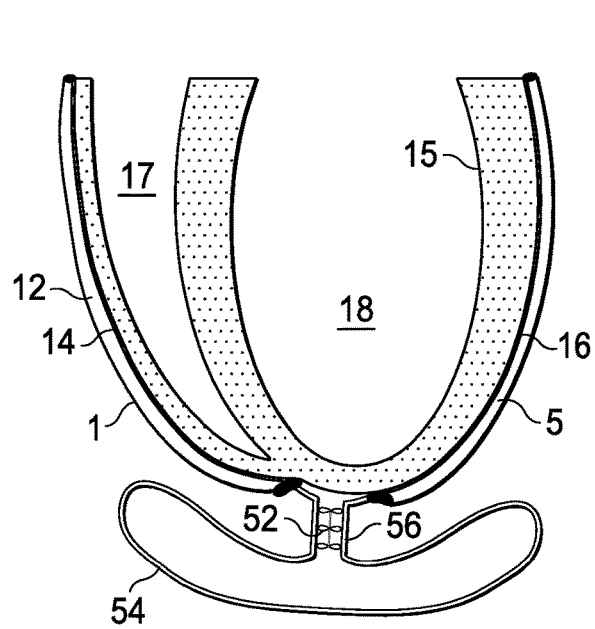
Figure 4B:
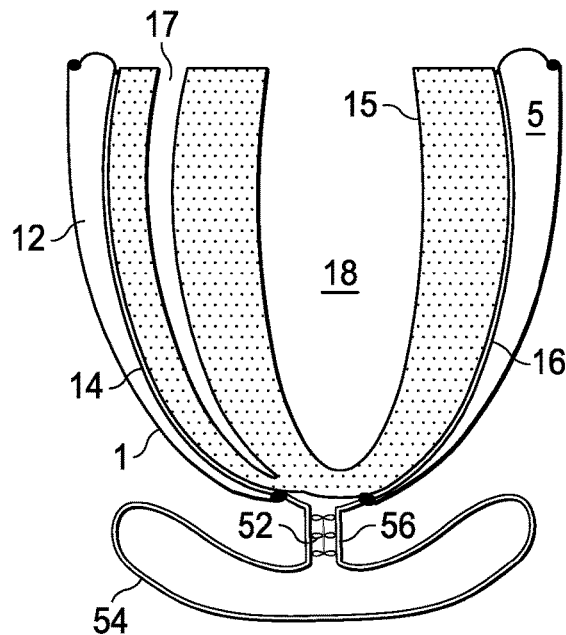

FIGS. 4A and 4B illustrate a vertical cross-section of one embodiment of the cardiac compression device 1 fitted to the heart 15 in the deflated state as seen in FIG. 4A and the inflated state as seen in FIG. 4B. Cardiac compression device 1 includes chambers 5 and 12 in the inflated and deflated states using fluid reservoir 54 (not shown). The interior surface 14 of the chambers 2-13 that are on the outer boundary form a shape that is similar to the end diastolic shape of the heart. The interior surface 14 has folds and crenulations such that when inflated the chambers 2-13 mostly expand inward to contact the epicardium 16 of the heart 15. The shape of the interior regions 17 and 18 can be compared in the inflated state as seen in FIG. 4B and the deflated state as seen in FIG. 4A.

The fully pressurized shape without the heart inside is helpful for illustrating one embodiment of the present invention, yet the shape will be significantly different when the device surrounds a heart which contains blood under pressure as seen in FIGS. 1B and 4B. With a heart inside, the pressure in the lumen of the device is higher than the pressure in the inflatable chambers. Because the chambers cannot fully expand, the inner film of the chambers is not taut. Rather than being supported by tension in the film, e.g., FIG. 1B, pressure on the lumen side of the longitudinal chambers is supported by contact forces on the epicardial surface, e.g., FIG. 3B. Without tension on the inner film, the attachment points are not drawn inward, e.g., FIG. 1B. Instead, the shape of the outer sides of the chambers becomes circular to support the pressure within the chambers, e.g., FIG. 3B. Note how the inner membrane is crenulated and thus, not under tension. Consequently, the pressure in the device chambers applies direct pressure to the heart surface. In a similar manner, a blood pressure cuff applies direct pressure to the surface of a patient's arm.

Because the inflatable chambers taper as they go from base to apex in a manner that resembles natural cardiac curvature as seen in FIG. 2B, the apex of the heart will have a physiological curvature. Moreover, because the device is rigid when pressurized, the curved shape of the apical end will act to prevent the heart from being expelled from the device. Basically, for the heart to leave the device the apical shape would have to pucker or a vacuum would need to form in the apical end of the device, both of which are unlikely.

At end-systole of the cardiac cycle, the present invention has a shape with curvatures that are similar to the proper end-systolic shape of the heart. The present invention is active in the sense that energy is consumed to accomplish the shape change during systole and energy is liberated to accomplish the shape change during diastole. The energy source is from a pneumatic pressure source. During systole (i.e., shape change from end-diastole to end-systole) the device is inflated with a positive pressure. During diastole (i.e., shape change from end-systole to end-diastole) the device of the present invention is deflated via suction. If enabled for RV flow restriction, the device of the present invention is not fully deflated during diastole because some residual pressure is applied to chambers that abut the right ventricle.

The present invention is soft or collapsible when deflated. In addition, the present invention minimizes the risks of thrombosis and infection, as there is no contact with the blood. Many of the devices in the art when pressurized or the end-systolic shape of prior devices is grossly abnormal and this is evidenced by the various schemes used to attach the cardiac compression device 1 to the heart (e.g., sewing to ventricle, basal drawstring, apical suction cup, etc.).

There is no need to attach the present invention to the heart because the heart is naturally drawn into the pressurized or activated device. Specifically, for the heart to leave the device (i.e., be extruded from the diastolic recoil device), the device curvature would need to invert, yet the device rigidity (when pressurized) resists curvature inversion. This is very useful because implantation time and complications due to attachment are minimized when this feature is present—i.e., when the activated shape of the device cavity (i.e., the inner wall of the diastolic recoil device which touches the epicardial or outer boundary of the heart) is nearly end-systolic shape. It can eliminate dyskinesis (defined as abnormal cardiac motions). Current evidence indicates that differentiation of cardiac stem cells into functional cardiomyocytes is influenced by mechanical stimuli such as the motion during cardiac contraction whereby the elimination of dyskinesis is of paramount importance. The device provides some of the pumping power demanded of the heart to energize or pressurize the circulatory system. Abnormal hearts often need to be "off-loaded" or be assisted with satisfying the circulatory demands of the body.

Figure 5:
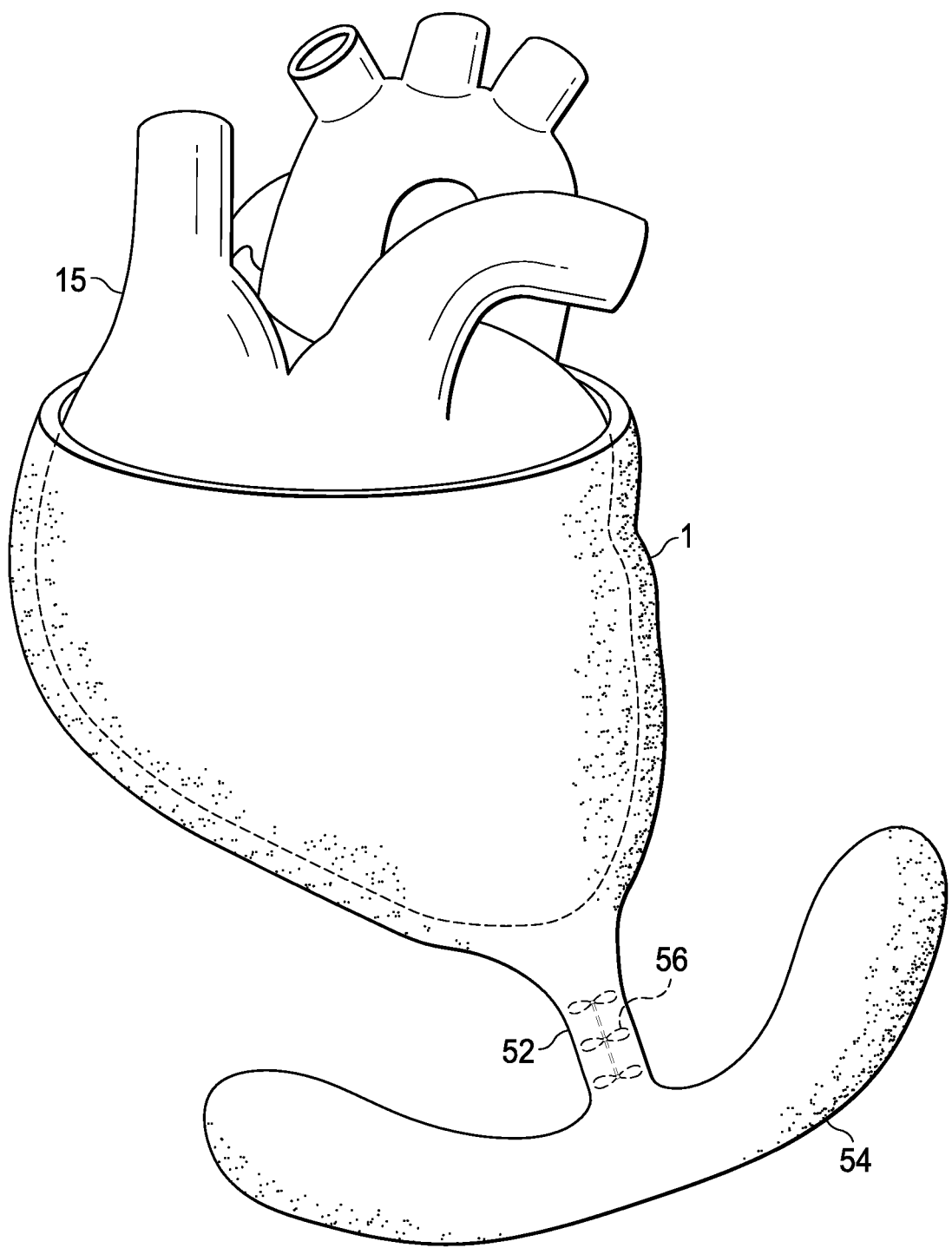
FIG. 5 illustrates one embodiment of the cardiac compression device that includes a cardiac compression device, channel and fluid reservoir.

FIG. 5 illustrates one embodiment of cardiac compression device 1 of the present invention that includes a cardiac compression device 1, channel 52 and fluid reservoir 54. The cardiac compression device 1 is fitted to the heart 15. The cardiac compression device 1 includes inflatable chambers arranged with chambers on the RV side and chambers that are mostly on the LV but also overlapping the interventricular sulci. The chambers (not shown) include interior surface (not shown) that contacts the epicardium (not shown) of the heart 15. The sides of the chambers (not shown) that are on the outer boundary form a shape that is similar to the end diastolic shape of the heart 15 (although in some embodiments the shape does not conform to the end diastolic shape of the heart). The inflatable chambers taper as they go from base to apex in a manner that resembles natural cardiac curvature as seen in FIG. 3B, the apex of the heart 15 will have a physiological curvature. The interior surface (not shown) has folds and crenulations (not shown) such that when inflated the chambers (not shown) mostly expand inward. Moreover, because the cardiac compression device 1 can be rigid when pressurized, the curved shape of the apical end (not shown) will act to prevent the heart 15 from being expelled from the cardiac compression device 1. Basically, for the heart 15 to leave the cardiac compression device 1, the apical shape would have to pucker or a vacuum would need to form in the apical end of the cardiac compression device 1, both of which are unlikely. A fluid driver 56 is in operable communication with the direct cardiac compression device 1 and fluid reservoir 54. One or more pressure regulators (not shown) may be included to regulate the pressure between the fluid driver 56 and the cardiac compression device 1 and/or the fluid driver 56 and the fluid reservoir 54. In addition, the fluid driver 56 may be in communication with a second fluid reservoir (not shown) and/or a power supply (not shown), a motor (not shown), controller (not shown) and/or pacemaker. The fluid reservoir 54 includes inlets/outlets (not shown) connected to the fluid driver 56 that can systematically introduce and withdraw a fluid (not shown) to and from the fluid reservoir 54 and cardiac compression device 1 in rhythm with the heart 15.

The fluid driver 56 causes an incompressible, low viscosity, biocompatible fluid, (e.g., air or saline, or low viscosity silicone oil) to flow in rhythmic pulsatile fashion into the fluid reservoir 54 and alternatingly into the cardiac compression device 1. The cardiac compression device 1 and the fluid reservoir 54 can be fully implantable within a patient to assist the beating of the patient's heart 15. The device can include a cardiac compression device 1, a fluid reservoir 54, fluid driver 56, control unit (not shown), a sensor, a regulator (not shown), a power supply (not shown) and a pacemaker (not shown) and can be fully or partially implantable subcutaneously in either the left or right chest or the upper abdomen.

The fluid driver 56 can be connected to a fluid reservoir 54 and controlled by a microprocessor in communication with one or more sensors that monitor and/or regulate the heart. In some embodiments, one or more check valves are in communication with the fluid driver 56. The cardiac compression device 1, fluid reservoir 54, and fluid driver 56 can each be constructed of at least one layer of material that is leak-proof, impermeable, and self-sealing. A prime volume of the fluid reservoir 54 can be predetermined based on a size of the patient and the fluid reservoir 54 can include an additional fluid volume to adjust hemodynamics. The fluid driver 56 can include a pump (not shown) directly attached to the motor or a pump remotely connected to a motor. The pump (not shown) can include a length of about three centimeters to about four centimeters and a diameter of about five centimeters, e.g., a length of 3.4 cm and a diameter of 5 cm. The pump (not shown) can use exotic materials including high purity thermoplastic. The pump (not shown) can include one or more impellers and a shaft constructed of a material including ceramic. In some embodiments, the motor (not shown) is a servo brushless direct current motor with a high starting torque and with a configuration to allow more space for coil winding. For example, the motor (not shown) can be a Series 1717 SR direct current micromotor with a precious metal commutator for use with a Series 16A spur gearhead, both manufactured by Faulhaber. The motor (not shown) can be powered by a rechargeable battery. In some embodiments, the one or more impellers may include elements of the rotor such as magnets and the stator may be positioned to surround the one or more impellers. In further embodiments, the one or more impellers may be magnetically suspended inside the stator housing. In some embodiments, the battery can be externally recharged by radio frequency through a coil external to the patient. The fluid driver (not shown) can operate according to one or more of the following parameters: a normal voltage of about 1 Volts to about 18 Volts, a power output of about 1-20 Watts, an efficiency of about 50-90 percent, and a maximum recommended speed of from 500 to 35,000 revolutions per minute. The fluid volume to inflate and deflate the cardiac compression device 1 can be controlled by the speed of the fluid driver 56. Changing the speed of the fluid driver 56 and the amount of fluid delivered, can allow adjustment of systolic pressure and can augment the function of the ventricles (not shown). Response to changing hemodynamic parameters can be in real time.

In some embodiments, the direction of impeller rotation may be periodically changed to reverse the direction of fluid flow and reverse the compression of the heart. In other embodiments, the impellers may be activated to start turning and cause compression of the heart. To remove compression of the heart, the one or more impellers may be stopped and allow the fluid to migrate away from the heart into the fluid reservoir 54, which may be configured to apply continuous vacuum on the fluid. Yet in further embodiments, the one or more impellers may be continuously activated for rotation and the direction of flow may be reversed via valves directing fluid to and from the one or more impellers.

The control unit (not shown) can regulate compression of the heart 15 by the aortic compression device and the direct cardiac compression device through communication with the pacemaker and the fluid driver. For example, a synchronized pacemaker (not shown) can regulate pulsatility of the compressions or the aortic compression device and the direct cardiac compression device. The control unit can regulate the compression and the decompression of the heart by the direct cardiac compression device. Synchronization by the control unit through communication with the pacemaker and the fluid driver can be based on dual-mode, dual-pacing, dual-sensing pacing, biventricular pacing, and/or three-chamber synchronization pacing. Pulsation ratios of inflation and deflation of cardiac compression device 1 can be adjusted on the basis of cardiac parameters, and the severity of the heart condition. A lower pulsation ratio can extend use of the rechargeable battery powering the control unit, sensors, fluid driver, pump, motor, and/or pacemaker. The pacemaker (not shown) can monitor the ECg of the heart 15 with one or more leads coupled to one or more of the right ventricle, the left ventricle, the right atrium, and the left atrium. The pacemaker (not shown) can be part of the control unit and include a processor that determines left ventricular cardiac parameters and right ventricular cardiac parameters. The cardiac parameters can include one or more of the following: left ventricular end diastolic pressure (LVEDP), left ventricular end systolic pressure (LVESP), right ventricular end diastolic pressure (RVEDP), right ventricular end systolic pressure (RVESP), left ventricular volume, right ventricular volume, cardiac tension, cardiac output, systolic blood pressure, diastolic blood pressure, and heart rate. The pacemaker can respond to changes in the cardiac parameters by changing the inflation rate, the deflation rate, and/or the fluid volume. In some embodiments, the pacemaker can continuously monitor and regulate cardiac hemodynamics in real time. The monitoring and regulating can be continuous and can immediately respond to changing cardiac hemodynamics. The pacemaker and/or control unit (not shown) can be programmed for mild, moderate, or severe heart disease.

Some embodiments of the invention include a device that is completely implantable, there is no interface with blood components that could cause coagulopathy or related morbidity, the patient can be completely ambulatory and physically active with the device implanted thus contributing to the quality of life, and expensive external monitoring to adjust the compression pressure is not required. Some embodiments of the invention respond to changing hemodynamics, which are constantly monitored. Embodiments of the invention are also cost effective in terms of initial insertions costs, subsequent hospitalizations, and follow-up costs.

The speed of fluid driver (which may include a kinetic or centrifugal pump, a peristaltic or positive displacement pump but may be of any type including axial turbine or a radial pump (not shown)) may be coordinated with a pressure regulator to create a sequence or series of wave forms or pulses of fluid in direct cardiac compression device to be rhythmically massaged or compressed. The regulation of pressures may be achieved by a relief valve coupled to the fluid circuit, a pressure regulator, or possibly, by "pump surge." Pressure regulator and pump are electrically coupled to a controller means or module, e.g., a microprocessor. The intensity of the compression step can be adjusted by adjusting the fluid driver, pump, pump speed and/or pressure regulator.

ECG-based or other heart event triggers are envisioned to be a part of the system (not shown) configured to provide the controller with reliable predictive or real-time information about the expected timing of systole and diastole of the heart.

The device may be battery-operated or be supported by an external electrical energy transmitted across the skin using transcutaneous energy transmission (TET) transmission coupling (not shown).

In its simplest operation mode, the driver may include an impeller, which is configured to first inflate the cardiac compression chamber at the beginning of systole by injecting drive fluid thereto. The drive fluid is removed from the fluid reservoir causing it to collapse. The systole of the heart will be therefore accompanied by the compression of the heart muscle externally. During diastole of the heart, the impeller may be reversed to cause deflation of the cardiac compression chamber and inflation of the fluid reservoir. In case of power failure, the system may be configured to deflate the cardiac compression bladders and inflate the fluid reservoir.

Figure 6:
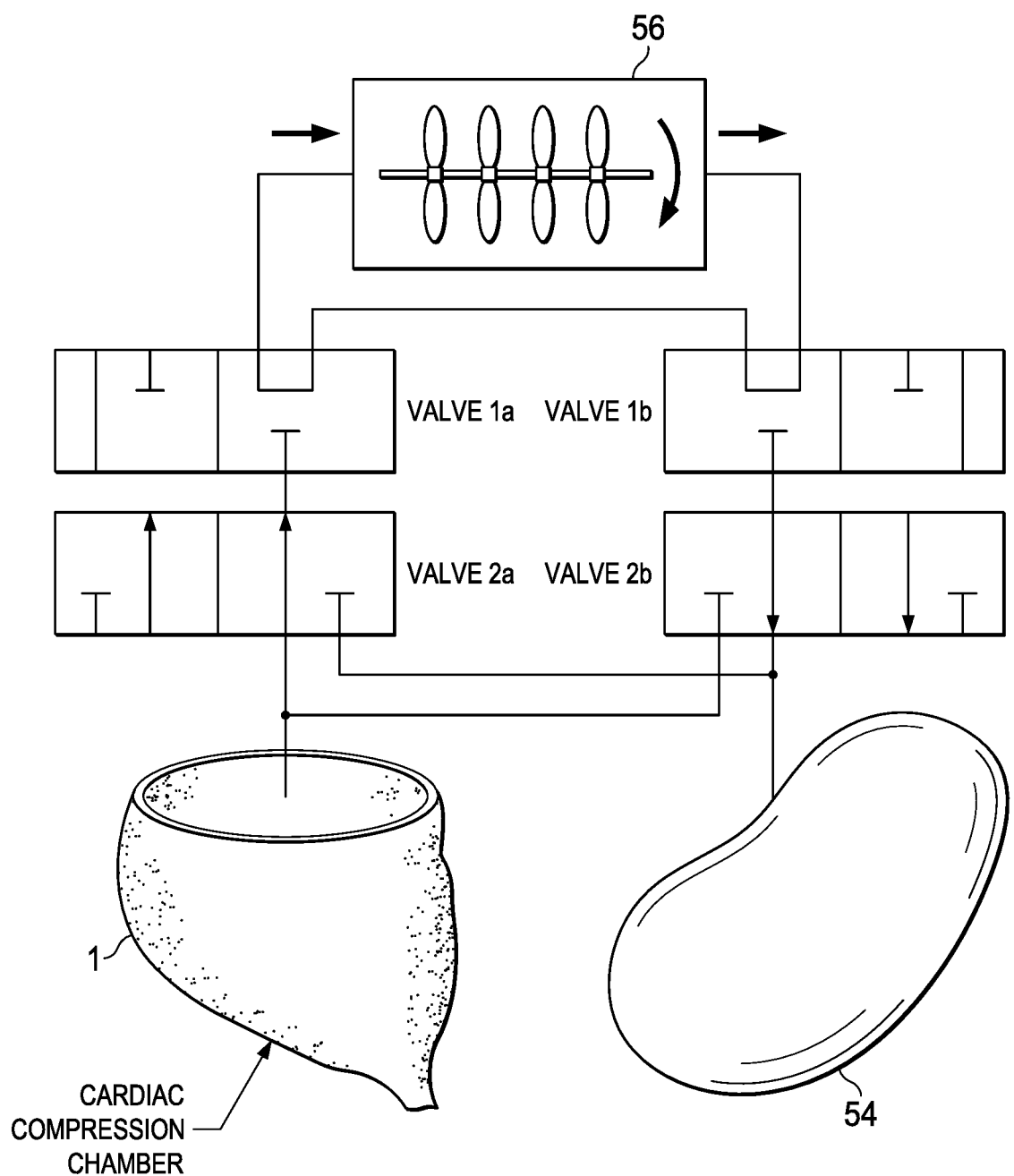
FIG. 6 illustrates a system that allows for a more sophisticated timing to be employed.

FIG. 6 illustrates a system that allows for a more sophisticated timing to be employed. Inflation and deflation of both chambers is desirable to be complete in the shortest time possible. Inertia of the rotating impeller may inhibit its fast reversal. To solve this problem, the device uses an impeller configured to rotate continuously in the same direction. A system of valves may be used to reverse the direction of the flow as well as to pause the flow of the drive fluid—without changing the direction or the speed of rotation of the impeller. The duration of systole as well as diastole may be longer than the time required to shift the volume of fluid from one chamber to the other. In order to unload the fluid driver 56 from having to exert continuous pressure and reduce the energy consumption, valves 1a and 1b are proposed to be included and configured to isolate the impeller from the chambers and the chambers from each other. Shifting valves 1a and 1b will reconnect the impeller to the chambers and allow the next phase of operation. Valves 2a and 2b are configured to reverse the direction of flow between the two compression chambers in order to reciprocate the drive fluid back and forth between the cardiac compression device 1 and the fluid reservoir 54 while maintaining the rotation of the impeller in the same direction.

Figure 7A:
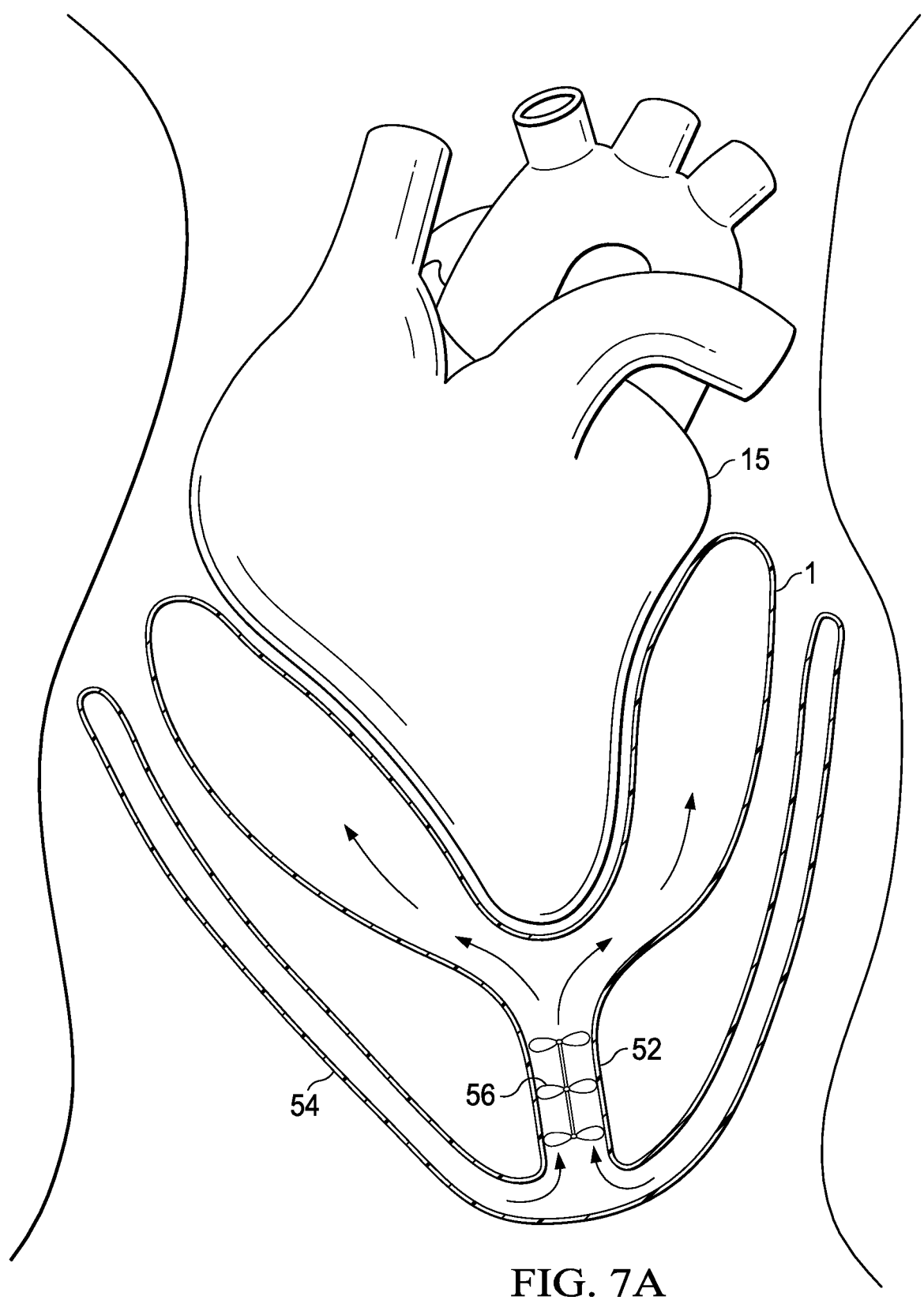
FIGS. 7A-7B illustrate a cardiac compression device that includes an inflated and a deflated cardiac compression device, channel and fluid reservoir.
Figure 7B:
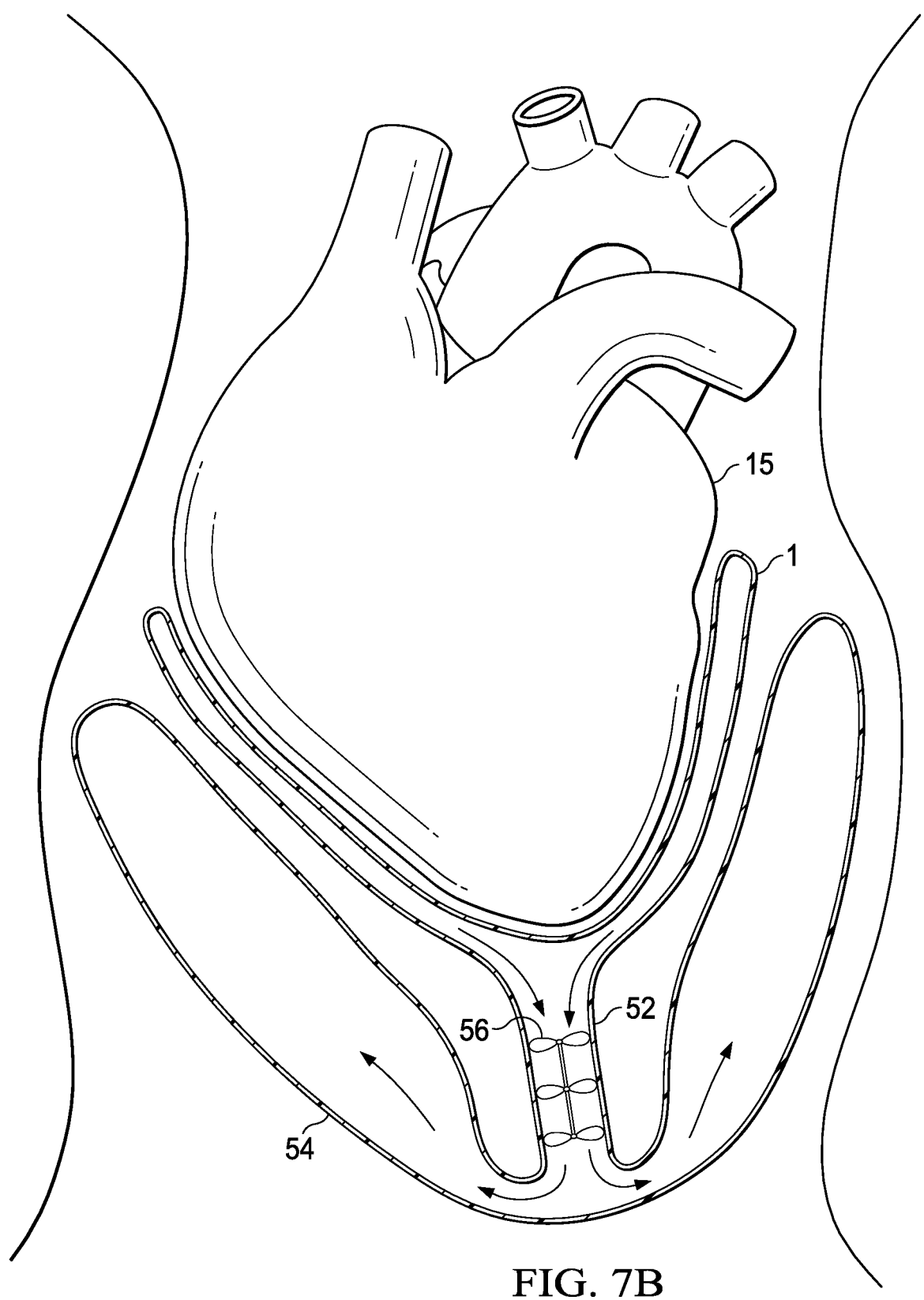

FIGS. 7A-7B illustrate one embodiment of cardiac compression device 1 of the present invention that includes a cardiac compression device 1, channel 52 and fluid reservoir 54. FIG. 7A illustrates a cardiac compression device that includes an inflated cardiac compression device 1 and a deflated fluid reservoir 54. FIG. 7B illustrates a cardiac compression device that includes a deflated cardiac compression device 1 and an inflated fluid reservoir 54. The cardiac compression device 1 is fitted to the heart 15. The cardiac compression device 1 includes inflatable chambers arranged with chambers on the RV side and chambers that are mostly on the LV but also overlapping the interventricular sulci. The chambers (not shown) include interior surface (not shown) that contacts the epicardium (not shown) of the heart 15. The sides of the chambers (not shown) that are on the outer boundary form a shape that is similar to the end diastolic shape of the heart 15 (although in some embodiments the shape does not conform to the end diastolic shape of the heart). The inflatable chambers taper as they go from base to apex in a manner that resembles natural cardiac curvature as seen in FIG. 2B, the apex of the heart 15 will have a physiological curvature. The interior surface (not shown) has folds and crenulations (not shown) such that when inflated the chambers (not shown) mostly expand inward. Moreover, because the cardiac compression device 1 can be rigid when pressurized, the curved shape of the apical end (not shown) will act to prevent the heart 15 from being expelled from the cardiac compression device 1. Basically, for the heart 15 to leave the cardiac compression device 1 the apical shape would have to pucker or a vacuum would need to form in the apical end of the cardiac compression device 1, both of which are unlikely. A fluid driver 56 is in operable communication with the direct cardiac compression device 1 and fluid reservoir 54. One or more pressure regulators (not shown) may be included to regulate the pressure between the fluid driver 56 and the cardiac compression device 1 and/or the fluid driver 56 and the fluid reservoir 54. In addition, the fluid driver 56 may be in communication with a second fluid reservoir (not shown) and/or a power supply (not shown), a motor (not shown), controller (not shown), and/or pacemaker. The fluid reservoir 54 includes inlets/outlets (not shown) connected to the fluid driver 56 that can systematically introduce and withdraw a fluid (not shown) to and from the fluid reservoir 54 and cardiac compression device 1 in rhythm with the heart 15.

Figure 8:
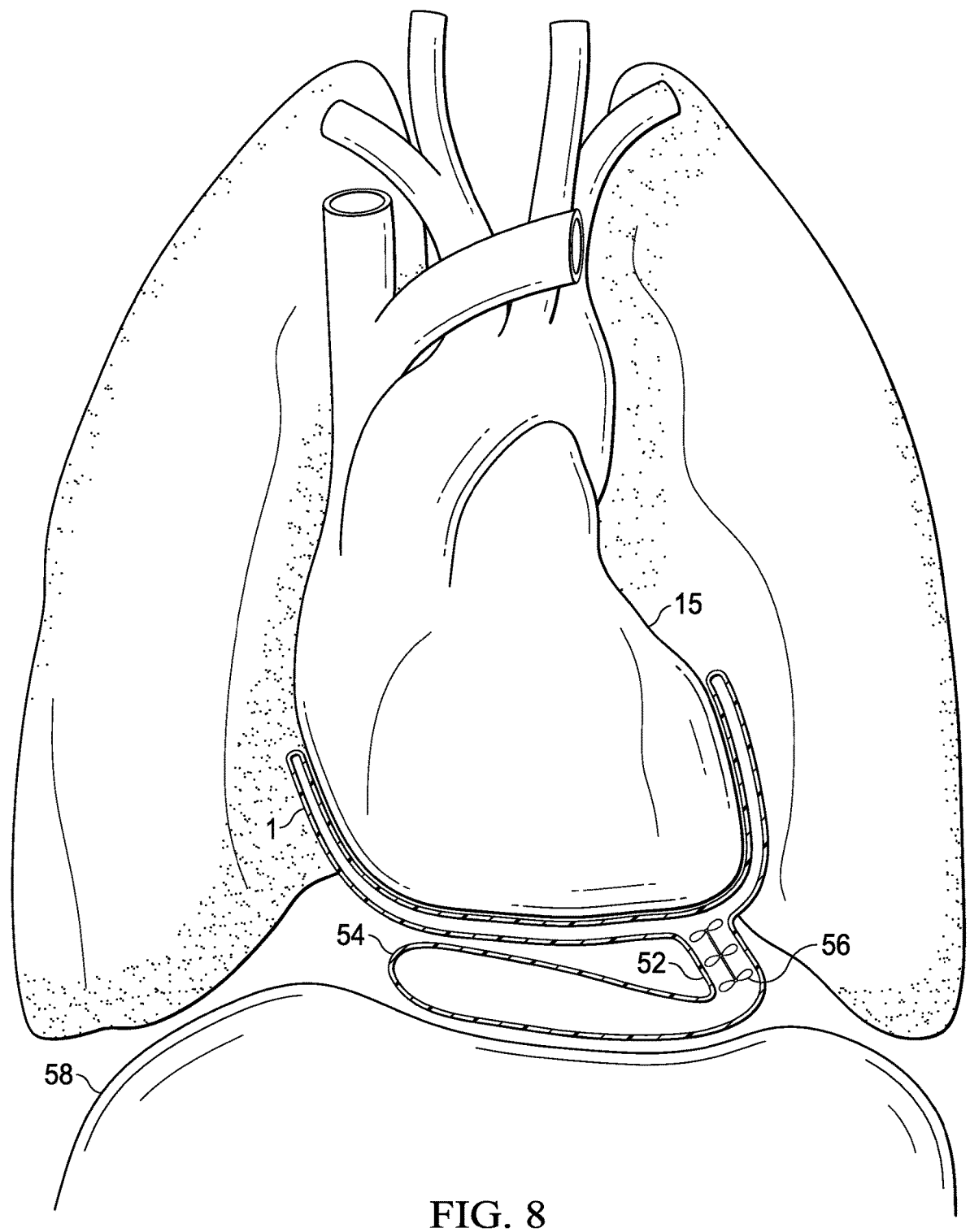
FIG. 8 illustrates a cardiac compression device that includes a cardiac compression device, channel and fluid reservoir that is positioned on the inferior margin of the pericardial sac between the heart and the diaphragm.

FIG. 8 illustrates cardiac compression device that includes a cardiac compression device 1, channel 52 and fluid reservoir 54 that is positioned on the inferior margin of the pericardial sac between the heart 15 and the diaphragm 58. The cardiac compression device 1 is fitted to the heart 15. The cardiac compression device 1 includes inflatable chambers arranged with chambers on the RV side and chambers that are mostly on the LV but also overlapping the interventricular sulci. The chambers (not shown) include interior surface (not shown) that contacts the epicardium (not shown) of the heart 15. The interior surface (not shown) has folds and crenulations (not shown) such that when inflated the chambers (not shown) mostly expand inward. A fluid driver 56 in the channel 52 is in operable communication with the direct cardiac compression device 1 and fluid reservoir 54. One or more pressure regulators (not shown) may be included to regulate the pressure between the fluid driver 56 and the cardiac compression device 1 and/or the fluid driver 56 and the fluid reservoir 54. In addition, the fluid driver 56 may be in communication with a second fluid reservoir (not shown) and/or a power supply (not shown), a motor (not shown), controller (not shown), and/or pacemaker. The fluid reservoir 54 includes inlets/outlets (not shown) connected to the fluid driver 56 that can systematically introduce and withdraw a fluid (not shown) to and from the fluid reservoir 54 and cardiac compression device 1 in rhythm with the heart 15.

FIG. 9 illustrates cardiac compression device that includes a cardiac compression device 1, channel 52 and fluid reservoir 54 that is positioned on the lateral margin of the pericardial sac between the heart 15 and the left lung 60. The cardiac compression device 1 is fitted to the heart 15. The cardiac compression device 1 includes inflatable chambers arranged with chambers on the RV side and chambers that are mostly on the LV but also overlapping the interventricular sulci. The chambers (not shown) include interior surface (not shown) that contacts the epicardium (not shown) of the heart 15. The interior surface (not shown) has folds and crenulations (not shown) such that when inflated the chambers (not shown) mostly expand inward. A fluid driver 56 in the channel 52 is in operable communication with the direct cardiac compression device 1 and fluid reservoir 54. One or more pressure regulators (not shown) may be included to regulate the pressure between the fluid driver 56 and the cardiac compression device 1 and/or the fluid driver 56 and the fluid reservoir 54. In addition, the fluid driver 56 may be in communication with a second fluid reservoir (not shown) and/or a power supply (not shown), a motor (not shown), controller (not shown), and/or pacemaker. The fluid reservoir 54 includes inlets/outlets (not shown) connected to the fluid driver 56 that can systematically introduce and withdraw a fluid (not shown) to and from the fluid reservoir 54 and cardiac compression device 1 in rhythm with the heart 15.

The fluid reservoir may be of any size or shape convenient to be placed inside the abdominal cavity thoracic cavity or any other cavity in the body. The fluid reservoir includes an inflatable bladder having an external covering. In one embodiment the inflatable bladder may be as simple as a flexible bladder that can expand and contract as necessary. For example, the inflatable bladder may be made from a elastomeric composition that allow expansion and contraction or the inflatable bladder may include a first body portion, a second body portion and a flexure region joining the first and second body portions. The fluid reservoir may have a simple spherical shape, conical shape, kidney shape, bladder shape, rod shaped, cylindrical shape, complicated combination of shapes or other free form shape that best accommodated the cavity present in the body. In another embodiment, the inflatable bladder may have a protective external covering to prevent the contact of the inflatable bladder with the cavity as the inflatable bladder inflates and deflates. The protective external covering may have an overall spherical shape, conical shape, kidney shape, bladder shape, rod shaped, cylindrical shape, complicated combination of shapes or other free form shape that best accommodated the cavity present in the body. In addition, the external covering may include a coating that prevents adhesion, resists bacterial growth, releases one or more active agents, etc. Depending on the type of the inflatable bladder, the external covering may enclose the inflatable bladder; or in another embodiment the external covering may be positioned adjacent the first body portion and has a peripheral extent at least equal to the peripheral extent of the inflatable bladder flexure region. The inflatable bladder and the external covering are shaped such that the external covering restrains a part of the first body portion at or near the flexure region against displacement towards the external covering (outward displacement) past a predetermined limit but allows unrestrained displacement away from the external covering (inward displacement).

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An implantable cardiac compression device comprising:
   an inflatable cardiac compression device comprising a resilient inner panel in contact with a heart periphery comprising one or more membranes contoured to provide curvatures generally in the shape of the heart to affect the end-diastolic heart volume, an inflatable outer panel comprising a plurality of inflatable membranes positioned completely around the resilient inner panel to inflate to affect the end-systolic heart volume completely around the heart periphery, and a fluid connection in communication with the inflatable outer panel for inflation and deflation;
   an expandable fluid reservoir in communication with the fluid connection and is adapted to be positioned adjacent the pericardium and configured to house a fluid when displaced from the inflatable cardiac compression jacket; and
   a fluid driver operably connected to the inflatable cardiac compression jacket and to the expandable fluid reservoir, wherein the fluid driver is configured to fill the cardiac compression jacket with the fluid at least partially removed from the expandable fluid reservoir during systolic ejection by the heart and is further configured to fill the expandable fluid reservoir with fluid at least partially removed from the cardiac compression jacket during diastolic filling of the heart.

2. The device of claim 1, wherein the inflatable membranes are substantially inelastic.

3. The device of claim 1, wherein a fluid is disposed within the expandable fluid reservoir.

4. The device of claim 1, wherein the expandable fluid reservoir is adjacent the pericardium.

5. The device of claim 1, wherein the expandable fluid reservoir is sized to fit between the pericardium and at least one lung to compress the at least one lung when the expandable fluid reservoir expands.

6. The device of claim 1, wherein the expandable fluid reservoir is sized to fit around at least a portion of the pericardium.

7. The device of claim 1, wherein the expandable fluid reservoir is configured to expand in the thoracic cavity.

8. The device of claim 1, wherein the inflatable cardiac compression device comprises between four to twelve at least partially overlapped membranes connected to form a continuous outer edge.

9. The device of claim 1, wherein the resilient inner panel, the inflatable outer panel, the expandable fluid reservoir or a combination thereof comprise an elastomeric polyurethane, a latex, a polyetherurethane, a polycarbonateurethane, a silicone, a polysiloxaneurethane, a hydrogenated polystyrene-butadiene copolymer, an ethylene-propylene, a dicyclopentadiene terpolymer, hydrogenated poly(styrene-butadiene) copolymer, a poly(tetramethylene-ether glycol) urethanes, a poly(hexamethylenecarbonate-ethylenecarbonate glycol) urethanes or combinations thereof.

10. The device of claim 1, wherein the cardiac compression jacket, the expandable fluid reservoir or a combination thereof further comprises one or more resilient members comprise individually a metal, an alloy, a memory metal, a composite, a polymer, a plastic, a memory plastic, strands, yarns, strips, or a combination thereof.

11. The device of claim 1, wherein the cardiac compression jacket further comprises one or more sensors, one or more electrodes to sense electrical activity of the heart to provide pacing stimuli to the heart, one or more electrodes to provide an electrical shock to the heart for defibrillation, one or more electrodes to provide an electrical stimuli to the heart, or a combination thereof in contact with the compression cardiac device.

12. The device of claim 1, wherein the cardiac compression jacket, the expandable fluid reservoir or both comprise one or more bioactive agents selected from antimicrobials, antibiotics, antimitotics, antiproliferatives, antisecretory agents, non-steroidal anti-inflammatory drugs, immunosuppressive agents, antipolymerases, antiviral agents, antibody targeted therapy agents, prodrugs, free radical scavengers, antioxidants, biologic agents or combinations thereof.

13. The device of claim 1, wherein the one or more bioactive agents are disposed on a coating.

* * * * *